United States Patent [19]

Stoddart et al.

[11] Patent Number: 4,768,516

[45] Date of Patent: * Sep. 6, 1988

[54] METHOD AND APPARATUS FOR IN VIVO EVALUATION OF TISSUE COMPOSITION

[75] Inventors: Hugh F. Stoddart, Groton, Mass.; Gary D. Lewis, St. Clair Shores, Mich.

[73] Assignee: Somanetics Corporation, Troy, Mich.

[*] Notice: The portion of the term of this patent subsequent to Feb. 18, 2003 has been disclaimed.

[21] Appl. No.: 830,567

[22] Filed: Feb. 18, 1986

Related U.S. Application Data

[63] Continuation-in-part of Ser. No. 542,022, Oct. 14, 1983, Pat. No. 4,570,638.

[51] Int. Cl.$^4$ ................................................ A61B 5/00
[52] U.S. Cl. ...................................... 128/665; 128/664
[58] Field of Search ............................. 128/632–633, 128/664–665, 634, 666–667; 356/39, 43.5, 432

[56] References Cited

U.S. PATENT DOCUMENTS

| | | | |
|---|---|---|---|
| 4,223,680 | 9/1980 | Jobsis | 128/633 |
| 4,281,645 | 8/1981 | Jobsis | 128/633 |
| 4,423,736 | 1/1984 | De Witt et al. | 128/633 |
| 4,467,812 | 8/1984 | Stoller | 128/664 |
| 4,495,949 | 1/1985 | Stoller | 128/664 |
| 4,510,938 | 4/1985 | Jobsis et al. | 128/633 |
| 4,515,165 | 5/1985 | Carroll | 128/664 |
| 4,541,438 | 9/1985 | Parker et al. | 128/664 |
| 4,570,638 | 2/1986 | Stoddart et al. | 128/665 |
| 4,592,361 | 6/1986 | Parker et al. | 128/633 |
| 4,600,011 | 7/1986 | Watmough | 128/664 |
| 4,616,657 | 10/1986 | Stoller | 128/664 |
| 4,649,275 | 3/1987 | Nelson et al. | 128/664 |
| 4,651,743 | 3/1987 | Stoller | 128/664 |
| 4,655,225 | 4/1987 | Dahne et al. | 128/664 |

OTHER PUBLICATIONS

"American Journal of Clinical Nurtrition 40", Dec. 1984, pp. 1123–1130, A New Approach for the Estimation of Body Composition: Infrared Interactance.
"Journal of Food Science", vol. 48 1983, pp. 471–474, Determination of Moisture, Protein, Fat and Calories in Raw Pork, Beef by Near Infrared Spectroscopy.
"Journal of Food Science", vol. 49, 1984, pp. 995–998, Application for Near Infrared Spectroscopy for Predicting the Sugar Content of Fruit Juices.

Primary Examiner—Kyle L. Howell
Assistant Examiner—Angela D. Sykes
Attorney, Agent, or Firm—Price, Heneveld, Cooper, DeWitt & Litton

[57] ABSTRACT

The specification discloses a method for determining the nature (e.g., physiological and compositional state) of internal tissue or other such biological material within a human organ or extremity, or other such individual examination subject, by use of selected light energy spectra. The selected light energy is applied to infuse the light throughout the interior of the area to be examined and the relative intensities of the infused light spectra are detected after having traversed the interior of the examination area. The detected intensities are computer-analyzed in a manner which conditions the raw magnitudes initially detected on the basis of the internal distance traversed by the infused light energy and also on the basis of broad averages of such conditioned wavelength-specific detection data representative of a number of comparable examination subjects. The resulting conditioned data is then plotted or otherwise comparatively analyzed, and the data profile so provided is shown to characterize the internal tissue structure and compositional state, showing relative amounts of particular different organic substance (e.g., fibro-glandular tissue, fat, hemoglobin, protein-bound water, etc.). Normative data profiles are prepared for specified age groupings, for comparison with corresponding data from individual subjects within such age groupings, whereby departures from the norm are graphically illustrated and revealed. The conditioned data also provides numeric quantification characterizing the relative different amounts of different tissue found to be present in a given test subject.

30 Claims, 4 Drawing Sheets

METHOD AND APPARATUS FOR IN VIVO EVALUATION OF TISSUE COMPOSITION

CROSS-REFERENCE TO RELATED APPLICATIONS

This application is a continuation-in-part of Applicants' co-pending application Ser. No. 542,022, filed Oct. 14, 1983, now U.S. Pat. No. 4,570,638, and is related to Applicants' co-pending application Ser. No. 827,526, filed Feb. 10, 1986, which are incorporated herein by reference.

TECHNICAL FIELD

This invention relates generally to optical response apparatus and methodology, i.e., the utilization of light energy as an investigative media in consideration and/or evaluation of internal tissue condition or state, accomplished by the infusion of specially-selected and/or specially-applied light energy into the tissue to be evaluated or analyzed and the resultant determination of the particular optical response of the subject to such light energy. Somewhat more particularly, the invention relates to diagnostic or clinical investigative apparatus and methodology which utilizes selected light spectra to assess the physiological state or condition of biological material, e.g., tissue, bone, etc., particularly on an in vivo and in situ basis, from the standpoint of transmissivity, or transmissibility, of the subject to the selected light spectra which are applied. Particular examples of apparatus and methodology exemplifying such investigative procedures are those disclosed in Applicants' above-referenced copending applications for U.S. Pat., including Ser. No. 542,022 (now U.S. Pat. No. 4,570,638) and Ser. No. 827,526, filed Feb. 10, 1986, both of which are incorporated herein by reference.

More particularly still, the present invention relates to the novel treatment (processing), interpretation, and presentation of optical response data obtained from examination of matter, particularly biological material, and especially including living tissue, in particular live human anatomical tissue, for example the internal tissue of the human breast.

BACKGROUND OF THE INVENTION

In Applicants' above-referenced and incorporated co-pending applications for U.S. patent, novel apparatus and methodology are disclosed for examining and appraising the physiological or compositional state or condition of, biological (organic) material; in particular, for conducting in vivo examination and assessment of the physiological state or condition of human tissue, for example diagnostic examination of the breast (or other anatomical portion) of live human subjects.

In accordance with the above-noted referenced and incorporated methodology and apparatus, selected light spectra are introduced into the subject being examined at selected locations, and the light energy so infused is then received (e.g., detected) at other particular locations, preferably including a pair of such other locations, for example, a "near" location closer to the point of light infusion and a "far" location disposed more remote from that point. As described more fully in the referenced co-pending applications, the use of at least two such receivers and the distances between the point of initial light insertion and the points of light reception are important factors in the useful application of the resulting data (i.e., the measured values of light intensity as determined by the detectors themselves).

Thus, the "optical probe" by which the optical response data is obtained incorporates means whereby the particular distance between the two optical "heads" (i.e., the light-producing and the light-receiving instrumentalities) may be determined in any given position to which the two such heads are adjusted to accommodate the size of a particular subject of examination. Such distance determinations, which may be designated "nominal optical distances", are inputted into the computing apparatus which is used to process the data, where they are utilized with other computation processes to "condition" or convert the "raw" data from the detectors so that it becomes representative of the intrinsic internal tissue composition of the subject under examination, i.e., independent of factors such as specimen (e.g., breast) thickness and boundary effects (e.g., skin pigmentation, etc.).

Such "conditioned" data, representative of intrinsic internal physiological state or condition, is of great value in portraying and understanding the actual internal nature of the particular tissue under examination, and a particularly useful manner in which such tissue characterization may be presented and apprehended is, as disclosed in co-pending application Ser. No. 542,022 ( now U.S. Pat. No. 4,570,638) by way of graphical presentations which constitute, in effect, spectrally-based, optical "profiles" of a given patient or other subject. As noted in this patent, such profiles may be visually contrasted in different ways with other such profiles, whether representative of the same patient or subject or other patients or subjects. For example, in human breast examination, comparison may be made to other profiles taken at adjacent or related positions on the same breast, and in contralateral studies, where profiles taken at the same locations on opposite breasts of the same patient are compared to one another. Additionally, such "profiles" may very advantageously be compared with other analogous profiles taken from other patients, whereby variations and abnormalities may be noted and taken under consideration.

SUMMARY OF THE INVENTION

The present invention carries forward the teachings and methodology presented in the above-referenced, incorporated, prior and co-pending applications, in particular that which is the subject of Applicants' prior and co-pending application Ser. No. 542,022, now U.S. Pat. No. 4,570,638. More particularly, the present invention discloses further attributes and novel utilization of the aforementioned "conditioned" light intensity data received at the aforesaid pair of locations ("near" and "far", or otherwise selectively located) on the subject being examined, in accordance with which the conditional state of the subject under study may be apprehended, and analytically defined, and considered on the basis of particular tissue or structure type, content, and related condition.

Accordingly, by use of a time-spaced chronology of such comparative characterizations, the progression of tissue changes in the subject may be specifically apprehended and evaluated on a continuing basis, toward the end that various norms of such progression may be apprehended and appreciated, and further toward the end that variations from such norms in specific patients may be observed and taken into consideration in treatment of the subject. Thus, the invention contemplates a more extensive as well as deeper understanding of the examination subject together with early screening and detection of anomaly and, accordingly, contemplates the possibility of increased early warning of the advent of non-characteristic changes which may signify the presence or onset of disease, degradation, or other such undesirable internal condition.

Still more particularly, the present invention contemplates, and provides, for the further "conditioning" of the spectrally-based optical response data referred to above, together with the preparation and presentation of further patient or subject "profiles" based upon such further conditioned optical data, in accordance with which internal metabolic and tissue characteristics and conditions may be apprehended, including for example relative presence within the interior of the subject being evaluated of such characteristics as hemoglobin content, water content, fat content, and fibrous tissue content.

Accordingly, the present invention provides methodology and apparatus in accordance with which the existing physiological or conditional state of a patient or other subject may be appraised on an ongoing metabolic basis, without use of any invasive agency or any ionized radiation, with the tissue or other substance being observed on an in vivo and in situ basis without disruption or modification of natural processes or state. The resulting information may be taken periodically from the same patient, and observed on a time-comparative basis, and/or it may be compared to normative values, prepared from large populations, for rapid, accurate and consistent diagnostic evaluation or analysis of the current state of the patient or subject under consideration in a manner unlike any other known instrumentality presently in comparable use.

The advantages provided and objectives satisfied by the aforementioned improvements will become more apparent and better understood by reference to the ensuing specification, which describes certain preferred embodiments to illustrate the underlying concept, together with reference to the appended drawings depicting the particularities of such preferred embodiments.

DETAILED DESCRIPTION OF PREFERRED EMBODIMENTS

Figure 1:
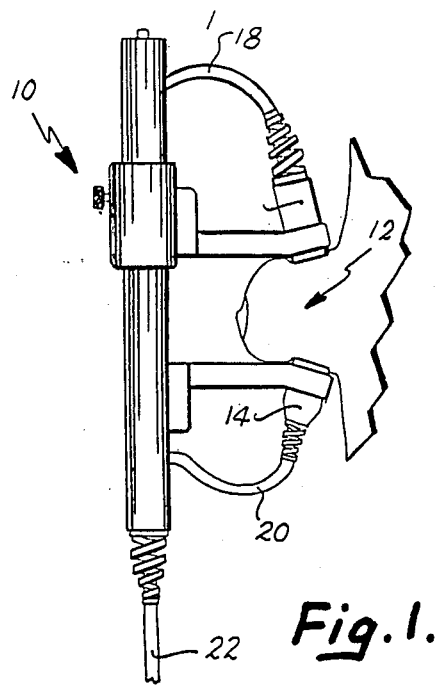
FIG. 1 is a fragmentary, pictorial side elevational view showing the general manner in which the optical examination instrument is utilized in obtaining optical response data from a given subject (here, the human breast) in accordance with Applicants' co-pending applications.
Figure 2:
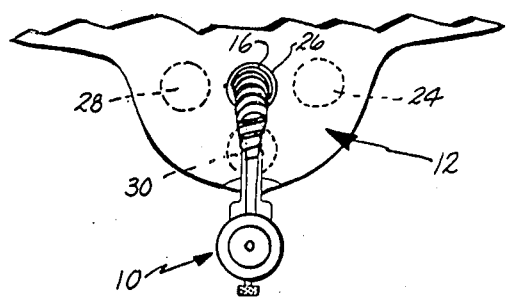
FIG. 2 is a fragmentary, pictorial overhead plan view of the subject matter shown in FIG. 1.

FIGS. 1 and 2 illustrate in a pictorial and generalized manner the basic aspects of the method and apparatus by which optical response data is preferably obtained for use in accordance with the invention, such method and apparatus being disclosed in detail in the aforementioned referenced and incorporated co-pending patent applications on behalf of Applicants. Somewhat more particularly, FIGS. 1 and 2 show the use of an optical "probe" 10 to examine (i.e., obtain optical response data from) a selected subject, in this case a human breast 12. In so doing, optical heads 14 and 16 of the probe 10 are lightly but firmly pressed against the top and bottom surfaces of the breast 12 sufficiently to provide good optical coupling, whereupon a sequence of light pulses of different wavelengths ranging over a selected spectrum is applied and the resulting intensity of the light energy infused into the breast is detected, preferably by both of the optical heads 14 and 16. As will be understood, the optical probe 10 is connected to a control console (not specifically illustrated) by cables 18, 20, and 22, by which suitable excitation (optical and/or electrical) is supplied and by which the optical response data is coupled to dataprocessing apparatus (e.g., a digital computer) located at the control console.

FIG. 2 illustrates the preferred placement and positioning of the optical heads during the overall examination, i.e., optical heads 14 and 16 are preferably moved sequentially to each of four different selected positions, designated by the numerals 24, 26, 28, and 30, respectively. Each such position constitutes a separate stage in the overall examination; i.e., the same sequence of selected light wavelengths is applied and resultant light intensity is detected at each of the four different locations. In the case of each breast (where breast examination is the particular application of the disclosed method and apparatus), examination positions 26 and 30 are generally aligned over the breast centerline, with position 26 being close to the chest wall and position 30 being remote from the chest wall, immediately behind the areola. One of the positions 24, 28 is thus disposed along the inner aspect of the breast while the other is disposed along the outer aspect.

As discussed at length in the referenced copending application Ser. No. 542,022 (now U.S. Pat. No. 4,570,638) of which the present application is a continuation-in-part, the optical response data produced in the general manner noted above thus consists of a sequence of electro-optical light-detector output values obtained at each of the different examination positions, each individual such detector output value comprising one individual point in the sequence of which it is a part, and corresponding to the amount of resultant light intensity detected at a particular examination location in response to the infusion of one particular wavelength (or narrow band thereof) in the applied spectrum. Generally speaking, these selected wavelengths comprise the visible and near-infrared spectrum extending approximately from 0.515 microns to somewhat beyond 1.2 microns and, as discussed more particularly below, this spectrum is preferably divided into on the order of about twenty to thirty specific examination wavelengths. As a consequence, the resulting optical response data corresponding to the light energy received at each of the different examination locations comprises a corresponding sequence of electrical pulses comprising detector output magnitude values (which may be considered the "raw" data).

As further explained in the aforementioned copending application Ser. No. 542,022, now U.S. Pat. No. 4,570,638, the "raw" detector output data just noted, while constituting a quantified (i.e., numerically designated) value which could be compiled and graphically plotted, and studied in various ways, is nonetheless preferably "conditioned" in several particular ways before being presented in the graphic optical response "profiles" shown in the aforementioned co-pending application which is now U.S. Pat. No. 4,570,638, examples from, which are also included in the drawings herewith, constituting FIGS. 3a, 3b, and 3c therein. In particular, two very significant "conditioning" factors are utilized, one of which is the particular separation distance between the two optical heads 14 and 16 which exists during each particular examination conducted. This dimension represents the "thickness" of the particular examination subject, and it is utilized with other known parameters (e.g., the "injected" or input light intensity and the "detected" or output light intensity received at a distant location on the examination subject) to compute the intensity reduction coefficient by use of the well-known exponential relationship expressing Beer's Law of intensity reduction across a given media thickness for a beam of light. This thickness or distance dimension is also (preferably) used to effect data conditioning by scattering and detector solid angle computation. Additionally, the optical response data is preferably further "conditioned" by in effect taking the ratio of the distance of thickness-conditioned data from a first light-receiver (e.g., one located at the optical head which also contains the light-emission apparatus, for example, optical head 16) with respect to the corresponding data from a second receiver (e.g., one which is located at the opposite optical head, i.e., head 14), which in the example shown is disposed at essentially the opposite side of the test specimen.

By so "conditioning" the raw detector output signals, a number of highly advantageous results are obtained, including the elimination of boundary effects (which, in the case of breast or other analogous examination, includes such skin characteristics or effects such as relative pigmentation, epidermal thickness, etc.), as well as in effect normalizing the data for the thickness of the particular examination subject. Accordingly, the resulting "conditioned" data is directly representative of intrinsic internal tissue composition and/or physiologic state, and it may be directly compared on a unit (i.e., numerical) basis to other such data, for example, comparable data taken from other examination locations on the same breast (or other such examination subject), or to data from the opposite such breast of the same patient, and indeed to data from totally different patients, with directly meaningful comparison results from which abnormalities and/or other characteristics may be discerned.

Figures 3, 3A, 3B, 3C:
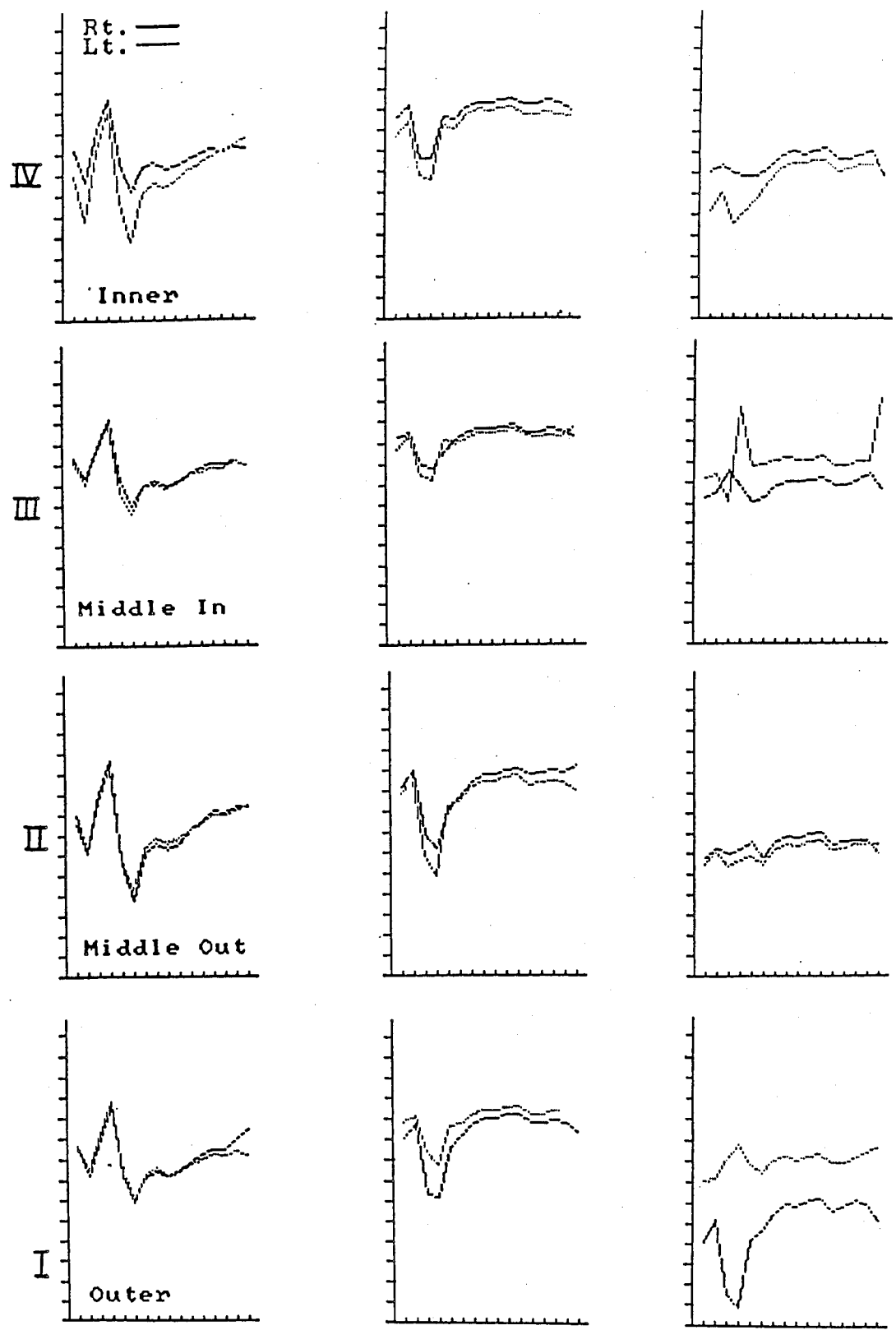
FIGS. 3a, 3b, and 3c are composite graphical presentations of optical response profiles taken from Applicants' co-pending application Ser. No. 542,022, now U.S. Pat. No. 4,570,638.

Accordingly, graphical "profiles" may thus be prepared from the resulting "conditioned" data to provide for highly meaningful comparison, and such profiles comprise the contents of FIGS. 3a, 3b, and 3c, which are repeated herein from Applicants' U.S. Pat. No. 4,570,638. In these figures, the different profiles in each horizontal row, designated "Inner", "Middle In", "Middle Out", and "Outer", respectively, correspond to optical response data obtained at the different examination positions 24, 26, 30, and 28, respectively (as illustrated in FIG. 2), and the vertical columns comprising FIGS. 3a, 3b, and 3c each represent different individual patients. Further, each individual graphical presentation or "profile" actually includes two superimposed traces, representing optical response data obtained at analogous positions on the two opposite breasts of the same examination subject, i.e., each such graphical representation constitutes a graphic contralateral comparison (as is also true of other such "profiles" shown in other figures and discussed hereinafter).

As may be observed from considering the different profiles of the three patients depicted in FIG. 3, as discussed above, particularly by contrasting the three different contralateral profile sets in any given horizontally aligned row thereof (representing the same examination location for each of the three different patients), vivid differences are clearly present and readily identifiable, on which diagnostic conclusions may be based. Nonetheless, in accordance with the present invention, valuable and meaningful enhancements are disclosed for the treatment of the "conditioned" optical response data on which the patient profiles are based. In particular, it has been discovered that optical profiles such as those illustrated in FIGS. 3a, 3b, and 3c may be reformulated into different and more meaningful presentations, from the standpoint of emphasizing certain features or characteristics and making them more readily identifiable. This is accomplished, in accordance herewith, by replotting the data in a manner reversing the axis direction (sense) for the abscissa and, more significantly, by expanding the abscissa scale (at least in the areas of greatest plot variation), i.e., taking a larger number of wavelength-related optical response data samples (and sampling at particular selected discrete wavelength choices), and enlarging the abscissa scale so as to spread out the more-detailed data. Even more significantly, the data is preferably further conditioned prior to graphical presentations. Such further conditioning of the data is accomplished by accumulating and averaging the above-described conditioned optical response data from numerous different examination subjects for each of the individual points on the graphical presentations ("optical profiles") (each such point corresponding to the conditioned data value at a particular examination wavelength), and then using the resulting broad-based average values of wavelength-related data points by subtracting from the corresponding conditioned current examination data values obtained during each new patient (or other subject) examination.

The subtractive procedure just noted has the effect of eliminating large, predominating, normative values for the wavelength-specific "conditioned" data and as a result amplifying or magnifying the remaining corresponding and related, but quite different, sequence of data values, which may then be graphically compiled and presented, or otherwise considered and evaluated. Further, the noted data cumulation and averaging may advantageously be carried out on the basis of chronological patient age groupings, such that the resulting "average" or "normal" data values which are subtracted from the conditioned examination values for a given subject are much more refined, and more specifically pertinent than would be true for a large "all ages" data base. Subtraction of these age-particular sets of "conditioned" data from the conditioned data of a particular individual under examination provides much more revealing data, from which a more revealing optical profile may be plotted, which is based upon age criteria and which is characterized primarily by specific departures from the norm or average for the age grouping of the particular examination subject being considered. Such data and corresponding profiles are, thus, highly representative of abnormality or eccentricity in the "intrinsic" internal tissue composition or state of the patient under examination.

The data base constituting such averaged values (whether on an age-related basis or otherwise) may and should be updated with each new patient or subject being examined, although it is to be noted that it is also desirable to eliminate from such data base the conditioned data (prior to the subtractive processing described above) for particular patients in which abnormalities are subsequently detected and proven, i.e., from patients having significant disease such as carcinoma which has been verified by subsequent diagnostic examination using such alternative media as mammography, ultrasound, and biopsy. Thus, the more the averaged data truly represents normative values, the more significant is the further-conditioned data brought about by the subtractive processing described above.

Figures 4, 4A, 4B, 4C, 4D:
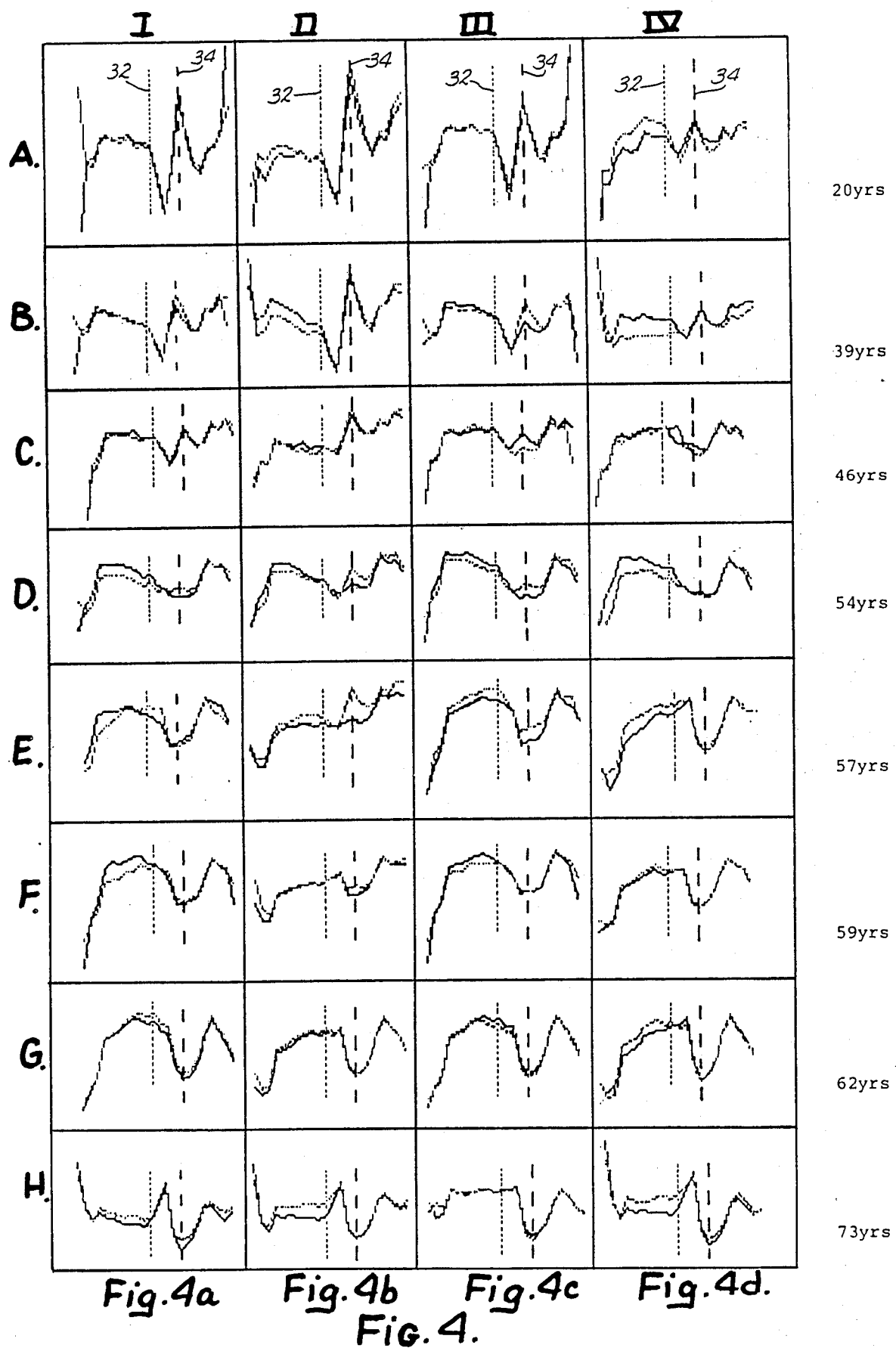
FIGS. 4a, 4b, 4c, and 4d are graphical presentations of optical profiles similar to those in FIG. 3, but based upon and incorporating refinements in accordance with the present invention.

The very substantial enhancements in optical profiles produced in accordance with the above-described further conditioning procedures may be appreciated by studying the content of FIG. 4, bearing in mind that the vertical columns of profiles in FIG. 4 compare to the horizontal rows of profiles in FIG. 3 (both designated by the numerals I-IV, inclusive); however, it must also be borne in mind that the graphical profiles of FIG. 3 are merely illustrative of randomly-occurring individual examination subjects, which include non-typical or anomalous physiological characteristics, whereas the profiles shown in FIG. 4 represent the averages of numerous "typical", or "normal", subjects. Of course, the four different sets of profiles in each horizontal row of FIG. 4 (designated "A", "B", etc.) represent each of the four different examination locations, and all of the profiles in each different horizontal row (of FIG. 4) correspond to a particular chronological age grouping for the associated patients or subjects (indicated in the right-hand margin of the figure).

Referring more particularly to the "average", or normative, profiles of FIG. 4, it is to be noted that profile includes a pair of mutually-spaced, vertically-disposed reference index lines designated by the numerals 32 and 34, portrayed by a series of dots in the one instance (index 32) and a series of dashes in the other instance (index 34). In each vertical column of profiles, index lines 32 and 34 are disposed in vertical alignment with one another, so that the reference points on the corresponding profiles from one horizontal row to another in a vertical column may readily be discerned and contrasted. Bearing this in mind, one may readily come to appreciate the information content present in the profiles of FIG. 4, both from the standpoint of the different examination locations of a given "average patient" at a given point in time, as well as from the standpoint of the same examination location for "average patients" of differing ages, considering each vertical column as proceeding (from top to bottom) in accordance with advancing chronological age. Accordingly, each of the different columns in FIG. 4, and in fact the entire figure as so construed, essentially characterizes in a direct, graphic manner, normative breast physiology changes which occur throughout a life cycle from 20 years of age to 73 years of age.

The different profiles of FIG. 4 contain information of considerably more significance than the generalized attributes referred to above. For a further consideration and better understanding of this significance, reference is made to FIG. 8 which, as labeled, shows a comparable pair of superimposed profiles 36 and 38, which characterize generally opposite types of human breast tissue content, as determined by professional medical examination utilizing the best available techniques (including mammography, ultrasound, and physical examination). Thus, profile 36 is characteristic of a human breast which has been medically determined as "99 percent fat", whereas profile 38 characterizes a human breast which has been medically determined as being "100 percent glandular". The differences in the corresponding profiles are readily apparent, profile 38 (characterizing the glandular breast) having a very prominent "peak" 39 which occurs at an examination wavelength where the other profile (36) has no corresponding such peak, and is instead in a relatively high valley. Further, profile 36, characterizing the fatty breast, has two notable peaks 35 and 37 which occur approximately the same distance on opposite sides of the highest peak 39 in profile 38, at points where the latter profile is in fact trending strongly downward. Apart from these areas, the two profiles are generally symmetrical, or at least analogously-contoured, although differing substantially in response magnitude (magnitude of the conditioned response data constituting the ordinate in each of the different profiles illustrated, with wavelength constituting the abscissa).

The significant peak 39 in the "100 percent glandular" profile 38 just noted is essentially centered upon index line 34, and the peak 35 in the fatty breast profile 36 appearing to the left of peak 39 is located approximately midway between index lines 32 and 34. The location of these indices (32 and 34) in FIG. 4 is based upon the considerations just noted, i.e., the particular location of the peaks 35 and 39 in profiles 36 and 38. While it may be appreciated that a third such index line could be utilized for the peak 37 in profile 36, it is not deemed necessary to do so for purposes of the present disclosure; however, it should be borne in mind that a peak occurring in any profile essentially midway between index lines 32 and 34 will characterize intrinsic breast tissue which is essentially fat in nature.

With the above-described nature of index lines 32 and 34 in mind, and referring back again to FIG. 4, the significance of the profiles there presented will thus become more clear. That is, considering for example horizontal row "A", which characterizes an essentially normal breast development in a twenty year old subject, it will be readily observed that strong (i.e., high) peaks are noted on index 34, and that the magnitude of such peaks varies from one location to another on the same breast at the same point in time, even though the two superimposed profiles representing the two opposite breasts of the same patient are quite comparable, particularly in the area of index 34. Somewhat similarly, the general shape of the plot at index is comparable in each of the different profiles in horizontal row "A", and it will be noted that index 32 in each profile marks the point at which the profile changes in general characteristic, describing a broad upwardly-directed "hump" to the left of index 32 and a precipitous, almost linear drop to the right of this index line.

Basically, the characteristics under discussion are the result of the combined effects of light intensity absorption by water within the breast tissue and scatter effects caused by the incidence of light rays upon the molecules which characterize the particular tissue state encountered. It should be noted, however, that the light-absorption and scatter characteristics attributed to different substances, such as hemoglobin, and the blood supply generally, within the vascular system being encountered are different than the effects attributable to other substances. More particularly, glandular tissue is largely characterized (optically speaking) by the presence of water molecules, although the particular parenchyma encountered, as well as the particular attendant stroma, will produce observably different optical response data for a number of reasons, including for example the nature of the molecular water bonding. At the same time, a somewhat opposite condition is present in the case of fat tissue, which contains little water and is largely "transparent" to incident light rays in the part of the spectrum here involved (although this is not the case in other parts of the spectrum).

Based upon the foregoing and other distinctions, a full appreciation of the optical response profiles set forth in FIG. 4 made possible by the present invention reveals the fact that the magnitude and shape of the profiles at index 34 is, as already indicated, an indication of the relative amount of glandular tissue present in the particular location being examined, whereas the shape and magnitude of the profile between indices 32 and 34 characterizes the fat content in each examination location, the shape and magnitude of the profile at and immediately to the left of index 32 characterizes the fibrous connective tissue which is present, and the area further to the left of index 32 generally characterizes the hemoglobin presence in the tissue at the corresponding examination location (the transmissivity characteristics of hemoglobin generally being known or available heretofore, both with respect to oxygenated and reduced hemoglobin, although not in terms of Applicants' substantially modified or "conditioned" optical data).

With the foregoing criteria in mind, further consideration of each different column (I-IV, inclusive) in FIG. 4 will reveal that these profiles show, and quantitatively characterize, the physiological and compositional state of internal human breast tissue through the life span of 20-73 years (bearing in mind that such profiles are believed to characterize "normal" conditions). Thus, the strong peak present at index 34 in row "A" (for example), typifying the relative extent and location of glandular tissue (as shown by the differences from one examination location to another for the same patient at the same age), will be seen to diminish perceptibly, if perhaps not precipitously, between ages 20 and 39, but that following that point in time the particular extent of glandular tissue present in each of the different locations diminishes to a marked and substantial degree, changing from a positive upward peak marginally present in the 46-54 year period (particularly in columns II and I, respectively, which characterize the area immediately behind the areola and extending to the outer aspect of the breast) to the opposite (downwardly-peaking) characteristic in succeeding years. Conversely, the fat content of the internal breast tissue gradually increases throughout this entire period, indicating in a clear and graphic manner the physiological generality that glandular breast tissue gradually atrophies and diminishes with advancing age and is steadily replaced by fat molecules. Analogous characterizations may be drawn with respect to index 32, characterizing the presence of fibrous connective tissue (stroma), and also the area to the left of index 32, characterizing hemoglobin.

With the foregoing criteria in mind, it may readily be appreciated that a particular optical profile resulting from examination of a specific individual will clearly show relative and comparative internal tissue characteristics actually present for that particular patient, and that a series of such profiles taken periodically over a span of years will show with great clarity and pertinence the "evolutionary" changes taking place in the internal tissue structure and composition of that particular patient during the aging process. Further, consideration of such profiles for a particular patient at any particular time in the life cycle on a comparative basis with nominal or "normal" profiles for the corresponding age grouping will clearly reveal the presence of anomaly, and it will also reveal the general nature and location of the anomaly as well. Due to the medical significance of the different criteria involved, as reviewed above, the presence or gradual onset of particular disease (e.g., carcinoma) is certainly likely to be apprehended. Of course, as disclosed in Applicants' prior and incorporated patents (particularly, U.S Pat. No. 4,570,638) the degree of symmetry, and variations therefrom, in the two superimposed traces of each profile, representing contralateral breast conditions, is extremely significant since the lack of symmetry is characteristic of diseased or other adverse physiologic state or condition. Thus, the divergence from complete symmetry in certain of the patient profiles set forth in FIG. 4 is suggestive of the possible presence of at least slight anomaly even in these "normative" profiles, although the relative variations in these profiles are observably slight.

Figures 5A, 5B, 5C, 5D:
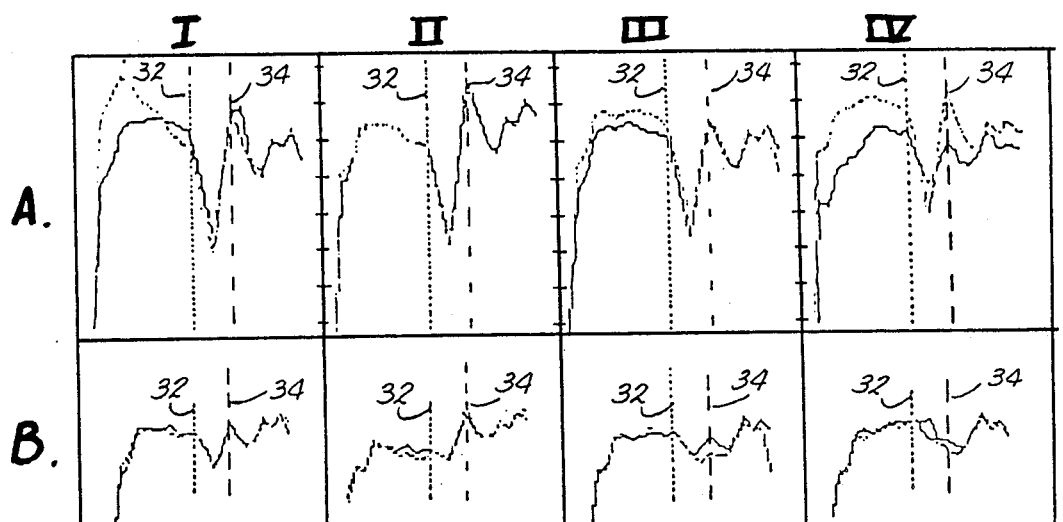
FIGS. 5a, 5b, 5c, and 5d are each two-part graphical presentations of optical response data of the general nature as that shown in FIG. 4, but depicting a "normal" response in juxtaposition to an "abnormal" response in comparable chronological age groupings.
Figures 6A, 6B, 6C, 6D:
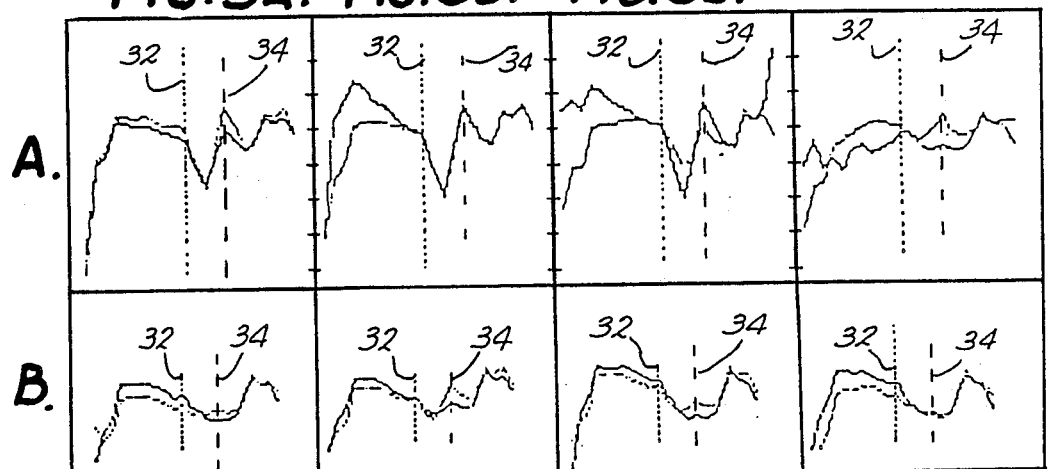
FIGS. 6a, 6b, 6c, 6d and 7a, 7b, 7c, and 7d are graphical presentations similar to those of FIG. 5, but depicting different subjects in different age groupings.
Figures 7A, 7B, 7C, 7D:
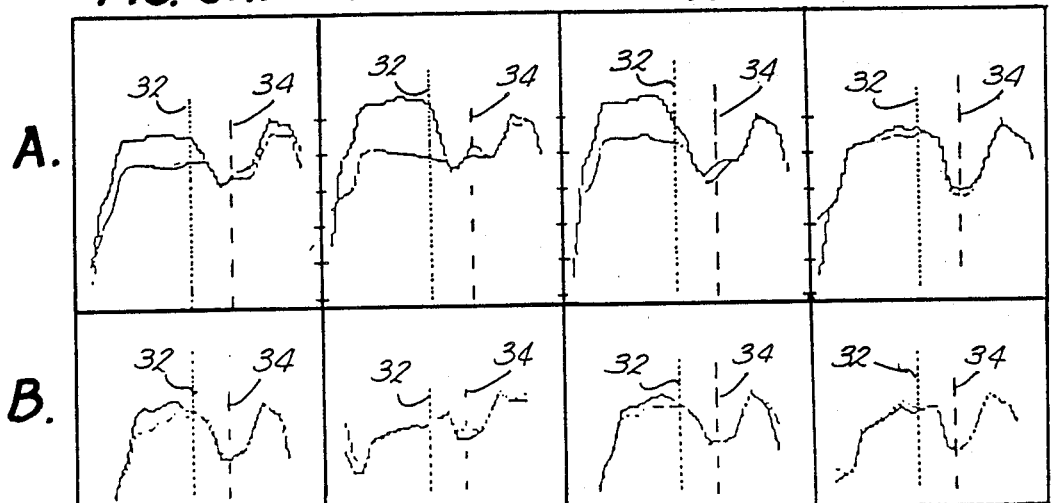

With the above factors and criteria in mind, consideration of FIGS. 5, 6 and 7 will further exemplify the significance and usefulness of Applicants' present invention. More particularly, in each of FIGS. 5, 6 and 7 the four vertical columns "I, II, III, and IV" (corresponding to FIGS. 5a, 5b, 5c, and 5d, etc.) characterize the different examination locations as referred to above (illustrated in FIG. 2); each of the three horizontal rows designated "A" are contralateral (two-trace) optical profiles taken from three different particular patients or examination subjects aged 47, 53, and 59, respectively, and the three horizontal rows designated "B" represent "normal" (actually, average) optical profiles for subjects of essentially the same chronological age as the subjects in corresponding rows "A". By comparing the shape of these correspondingly-displayed optical profiles (i.e., comparing the "A" and "B" profiles of FIGS. 5a, 5b, 5c, etc.), one may note the following.

With respect to FIG. 5, the subject under examination (row "A") has substantially greater peaks at both indices 32 and 34 than the norm for a patient of that chronological age, and the corresponding or correlative condition of a slight peak or rise present in the norm between these two indicia, characterizing fat content, is far less present in this patient, indicating that essentially no fat replacement has yet taken place even though a significant amount of such replacement is normal for this age. Additionally, the substantial degree of asymmetry evident in the region to the left of index line 32 is cause for definite concern, indicating increased vascularity (which will typically be associated with malignancy). In validation of these conclusions indicative of interior tissue anomaly, clinical medical examination of this patient by mammography produced a diagnosis of ductal hyperplasia, with bizarre calcification in the upper outer quadrant of the left breast, together with several large cysts. Biopsy showed intraductal carcinoma of the left breast.

Somewhat similarly, consideration of the optical profile for patient "A" in FIG. 6 shows substantial asymmetry, together with significantly higher peaks at index line 34 than would normally be present, as well as the generalized condition of very little fatty replacement of glandular tissue compared to that which would normally be present. Further, the extent of asymmetry between the two breasts (i.e., between the two traces in each view) in the area to the left of index 32 is immediately apparent, particularly in columns II and III, which represent the two positions in the center of the breast (i.e., positions 26 and 30 as shown in FIG. 2), where the profile for the right breast (i.e., the top trace) appears to show increased hemoglobin not present in the left breast, appearing to indicate significant additional blood supply to the area. Clinical medical evaluation of this patient resulted in a diagnosis of "apparently benign" lesion, with calcifications, at the center of the right breast; however, ensuing biopsy confirmed the presence of intraductal carcinoma of the right breast.

In FIG. 7, patient "A", an individual aged 59 years, shows evident asymmetry at, and to the left of, index line 32, particularly in columns I, II, and III (representing the outer aspect of the breast, the middle front position, and the middle back position, respectively), although the shape and nature of the profiles along index 34 is basically of normal appearance and, in fact, the entire profile in column IV (the inner aspect of the breast) is reasonably representative of the "normal" profile for this area. The evident asymmetries in the traces, and the apparently increased vascularity evidenced by the higher of the two traces in the area to the left of index 34 in columns I, II and III seem ominous, however, and tend to show a proliferation of fibrous tissue in this area which, with the increased vascularity noted, seemingly indicate widely-distributed anomaly which is likely to be malignant in the right breast. Medical examination of this patient concluded the presence of extensive and widespread carcinoma of the right breast notwithstanding the absence of any specific large mass (tumor). Ensuing biopsy verified that the patient had extensive and widespread "islands of malignant cells".

From the foregoing observations in conjunction with FIGS. 5, 6 and 7, it will be apparent that the Applicants have provided further novel and highly useful refinements of the methodology initially set forth in co-pending application Ser. No. 542,022, now U.S. Pat. No. 4,570,638, in accordance with which an understanding of ongoing metabolic changes and of actual physiologic state and composition may readily be achieved. In the first place, these enhancements and improvements embrace the concept of further conditioning of the optical response data in the manner described, i.e., by compiling an extensive optical response data base from which numerical averages may be drawn which are representative of average, and hence presumably normal, subjects in the general population. Additionally, the invention contemplates the interpretation and presentation of this data base on the basis of chronological age groupings which, as demonstrated above, have significant variance from one such grouping to another. The further conditioning of the optical response data in accordance with the invention, by subtracting the averaged, normative data from the optical response data for a particular patient, after conditioning of the patient data on the basis of specimen thickness and the ratio of near-to-far receivers, thus produces a different and much more expositive optical profile, which makes existing anomalies and the like more evident and more understandable, providing for highly meaningful graphic comparison to analogous normative optical profiles for corresponding age groupings. Ultimately, the methodology attributable to this invention provides for the direct apprehension, and assessment, of metabolic tissue composition and characteristics existing internally within the breast, on an in situ and in vivo basis, without any disruption whatsoever of normal structure or metabolic processes, and also without the use of any ionizing radiation or other invasive modality (such as, for example, X-ray, NMR, etc.).

Accordingly, the methodology of the present invention provides new and useful concepts for appraisal of the existing physiologic state, condition, and composition of examination subjects, even to the extent of learning the basic types of internal tissue or cell constituency present at the time of examination, enabling relative comparison of such constituencies from time-to-time, to determine changes at an early date. In this regard, it is to be noted that the relative height along the ordinate of the different points on the optical profiles signifies magnitude in a somewhat absolute sense, as well as merely providing a measure of relative asymmetry in contralateral studies of the same patient, since ordinal magnitudes of points on the optical profiles of specific patients may also be compared to ordinal magnitudes of the corresponding points on the profiles representative of "normal" (average) patients in the corresponding age grouping. Thus, it is entirely within the scope of the invention to ascribe highly specific and useful meaning to particular patient profiles which are basically symmetrical contralaterally and essentially correspond in shape to the average profiles for the particular age group but which vary significantly therefrom in particular location along the ordinate (even though such a condition would be rather unlikely, at least as just stated).

Figure 8:
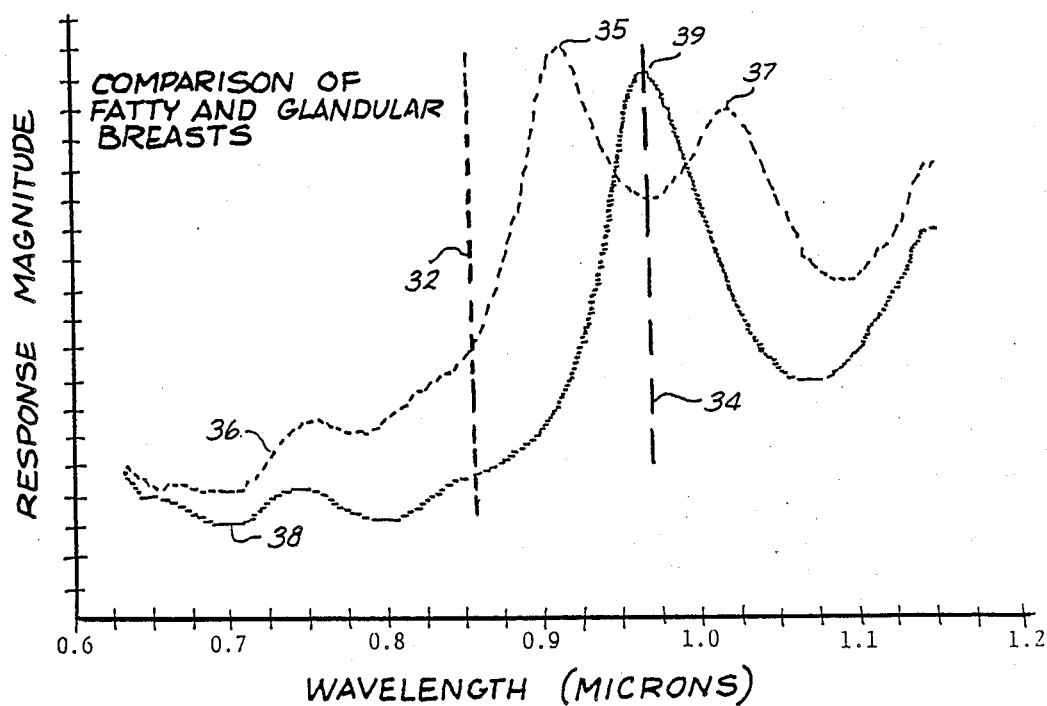
FIG. 8 is a graphical presentation of two superimposed sets of optical response characteristics typifying fatty versus glandular human breast tissue.

Of course, magnitude or ordinal position of the optical response profiles, together with graphical shape, are highly significant attributes of the methodology presented, and in this respect it is to be pointed out that while the general band of desired examination wavelengths has been identified above, and is generally indicated in FIG. 8, and the general number of desired optical data samples has been indicated, it is nonetheless to be noted that as a result of the findings described hereinabove the optical information obtained from examination in certain particular areas, (i.e., at particular wavelengths) is probably more meaningful than the data from other wavelengths. Accordingly, more widely-separated examination wavelengths may be used in the regions outwardly of and comparatively remote from index lines 32 and 34, but a larger number of more closely-spaced examination wavelengths are to be recommended in the general vicinities of these index lines and in fact throughout the bandwidth separating them. For example, while wavelength separation of perhaps 50 to 100 nanometers may well be satisfactory for examination in the areas substantially outward from index lines 32 and 34, in the closer vicinity to these indices it may be desirable to use separations of only about 25 nanometers (or less) between the examination wavelengths, in effect doubling or even tripling the number of samples obtained over comparable bandwidths centered upon these index lines, and perhaps throughout the area separating them. Additionally, the abscissa may be widened and the data from this spectral area amplified. By so doing, specific detail and contour in the optical profiles may be made more perceptible and more apparent, making possible a more critical and more meaningful analysis of the internal tissue characteristics being appraised.

It should further be expressly pointed out that while the primary subject matter of investigation described above in conjunction with the particular preferred embodiment discussed herein constitutes human breast examination and evaluation, it should be clearly understood that the underlying discoveries and technologies are not nearly so limited. That is, the same basic approaches are undoubtedly applicable to other in vivo, in situ organic subject matter, including not only a wide variety of other human organs or other defined anatomical areas, but also including a wide variety of other such biological materials or substances, to the extent the same are susceptible to optical response interrogation in the same or similar general manner.

It is to be understood that the above detailed description is merely that of certain exemplary preferred embodiments of the invention, and that numerous changes, alterations and variations may be made without departing from the underlying concepts and broader aspects of the invention as set forth in the appended claims, which are to be interpreted in accordance with the established principles of patent law, including the doctrine of equivalents.

The embodiments of the invention in which an exclusive property or privilege is claimed are defined as follows:

1. A method of assessing and classifying the physiological and compositional state of internal matter within an individual examination subject comprised of organic material and the like which is transmissible by at least certain selected light energy wavelength spectra, comprising the steps: applying the selected light energy spectra to each of a plurality of examination subjects including said individual examination subject in a manner which infuses at least certain of such light energy into the interior of each such subject; detecting the presence of said infused light after the same has transmissed at least a portion of the interior of each such subject; quantifying the detected light energy for each examination subject as a sequence of values correlated with at least certain of said selected wavelengths to thereby produce a sequence of discrete wavelength-related values for each such examination subject; conditioning said discrete values for each such examination subject at least partially on the basis of the distance within the interior of said subject transmissed by said infused light energy, to produce a series of wavelength-related individual conditioned quantified values particularizing the individual examination subject; determining an average of at least selected such individual wavelength-related values from at least certain of the plurality of series of wavelength-related individual conditioned quantified values obtained by examination of said plurality of examination subjects; further conditioning the series of wavelength-related individual conditioned quantified values for said individual examination subject by subtracting therefrom the said average determined from selected values in the series thereof for the plurality of examination subjects; and comparatively analyzing said further-conditioned series of wavelength-related individual values for said individual examination subject to assess and classify the composition of internal matter within the said individual examination subject transmissed by said infused light energy.

2. The method as set forth in claim 1, wherein said step of subjecting said further-conditioned values for said individual examination subject to comparative analysis includes graphically plotting such values.

3. The method as set forth in claim 1, including the step of determining said average from an examination subject population which is selectively chosen.

4. The method as set forth in claim 1, wherein said step of comparative analysis includes comparison of said further-conditioned series of wavelength-related individual examination subject values with an analogous plot of further-conditioned values which are generally normative of a class of examination subjects to which said individual subject is directly related in at least one characteristic parameter.

5. The method as set forth in claim 4, wherein said examination subjects comprise living beings and said characteristic parameter includes the chronological age of the individual examination subject.

6. The method as set forth in claim 5, wherein said step of comparative analysis includes the step of visual comparison of a plot of said individual examination subject values with said like plot of said normative values.

7. The method as set forth in claim 6, wherein said visual comparison is carried out at least in part by placing said plots in juxtaposed visual alignment with each other.

8. The method as set forth in claim 4, wherein said comparison includes the step of particularly comparing selected portions of said series of individual examination subject values which are representative of particular examination wavelengths selected from the totality of those applied to the examination subjects with subsantially same selected wavelength-represented portions of the series of normative values.

9. The method as set forth in claim 8, wherein said visual comparison is carried out visually at least in part by viewing graphical plots of at least portions of said series.

10. The method as set forth in claim 9, wherein said visual comparison is carried out at least in part by placing said plots in juxtaposed visual alignment with each other.

11. The method as set forth in claim 8, wherein said particular examination wavelengths include at least those within the band of from about 850 nanometers to about 1,000 nanometers.

12. The method as set forth in claim 8 wherein said particular examination wavelengths include at least those within the band of from about 950 nanometers to about 1,000 nanometers.

13. The method as set forth in claim 8 wherein said particular examination wavelengths include at least those within the band of from about 900 nanometers to about 950 nanometers.

14. The method as set forth in claim 8 wherein said particular examination wavelengths include at least those within the band of from about 850 nanometers to about 900 nanometers.

15. The method as set forth in claim 1, wherein said step of subjecting said further-conditioned values to comparative analysis is carried out with respect to values which are representative of examination wavelengths generally within the overall spectral band of from about 550 nanometers to about 1,200 nanometers.

16. The method as set forth in claim 1, and including the procedure of conducting contralateral comparisons for paired portions of an examination subject by subjecting each such portion to corresponding such wavelength-related examinations, to thereby produce paired series of said wavelength-related individual values, and conducting said comparative analysis at least in part by comparing one such series of values to the other.

17. The method as set forth in claim 16, wherein said step of conducting comparative analysis is further carried out by comparing said paired series of wavelength-related individual subject values with respect to other such series of values characterizing normative examination subjects.

18. The method as set forth in claim 17, wherein said examination subjects comprise living beings and said other such series of values characterizing normative subjects is selectively structural to represent a chronological age grouping which includes the age of said individual examination subject.

19. The method as set forth in claim 18, wherein said step of conducting comparative analysis includes graphically plotting at least certain of said series of values.

20. The method as set forth in claim 17, wherein said step of conducting comparative analysis includes the step of particularly comparing selected portions of said paired series of values which are representative of particular examination wavelengths selected from the overall spectrum which is applied to the examination subject.

21. The method as set forth in claim 20, wherein said particular examination wavelengths include at least those within the band of from about 850 nanometers to about 1,000 nanometers.

22. The method as set forth in claim 21, wherein said particular examination wavelengths include at least those within the band of from about 950 nanometers to about 1,000 nanometers.

23. The method as set forth in claim 16, wherein said step of subjecting said further-conditioned values to comparative analysis is carried out with respect to values which are representative of examination wavelengths generally within the spectral band of from about 550 nanometers to about 1,200 nanometers.

24. In a method of optically assessing the internal physiological characteristics of an individual examination subject which is comprised of matter transmissible by at least certain selected light energy wavelengths, wherein such light energy is applied to the subject so as to inject the light internally within the subject and injected light is detected at a location whose distance from that at which the light is injected is particularly determined, the process of assessing said internal characteristics which comprises the steps of classifying separate portions of said detected light as a function of particular wavelength groupings, and interpreting the amounts of detected light which are so classified as relative quantities of specific types of constituent matter which are particularly characterized by said particular wavelength groupings.

25. The method for optical methodology as recited in claim 24, wherein said step of interpreting including the comparison of said quantities of specific types of matter relating to an individual examination subject with normative quantities of such types of matter present in examination subjects of the general class to which such individual subject belongs.

26. The method for optical methodology as recited in claim 24, wherein said particular wavelength groupings comprise wavelengths within the band of from about 540 nanometers to about 1,250 nanometers.

27. The method for optical methodology as recited in claim 24, wherein at least one of said particular wavelength groupings comprises wavelengths within the band extending from about 950 nanometers to about 1,000 nanometers.

28. The method for optical methodology as recited in claim 24, wherein at least one of said particular wavelength groupings comprises wavelengths within the band extending from about 900 nanometers to about 950 nanometers.

29. The method for optical methodology as recited in claim 24, wherein at least one of said particular wavelength groupings comprises wavelengths within the band extending from about 900 nanometers to about 950 nanometers.

30. The method for optical methodology as recited in claim 24, wherein at least one of said particular wavelength groupings comprises wavelengths within the band extending from about 800 nanometers to about 850 nanometers.

* * * * *